United States Patent [19]

Goldberg et al.

[11] Patent Number: 4,526,781

[45] Date of Patent: Jul. 2, 1985

[54] HAIR CARE COMPOSITIONS

[75] Inventors: Marvin Goldberg, Monsey; Arthur Brandon, Valley Cottage, both of N.Y.

[73] Assignee: Revlon, Inc., New York, N.Y.

[21] Appl. No.: 603,864

[22] Filed: Apr. 25, 1984

[51] Int. Cl.$^3$ .......................... A61K 7/06; A61K 7/11
[52] U.S. Cl. ................. 424/70; 424/DIG. 1; 424/47; 424/78; 514/556
[58] Field of Search .................. 424/70, 316, DIG. 1, 424/47

[56] References Cited

U.S. PATENT DOCUMENTS

| | | | |
|---|---|---|---|
| 3,960,742 | 6/1976 | Leonard | 252/90 |
| 4,107,328 | 8/1978 | Michaels | 424/316 |
| 4,166,845 | 9/1979 | Hansen et al. | 424/78 |
| 4,221,733 | 9/1980 | Melloh et al. | 424/70 |
| 4,348,292 | 9/1982 | Ginn | 424/70 UX |
| 4,370,272 | 1/1983 | Wechsler et al. | 260/404 |
| 4,375,421 | 3/1983 | Rubin et al. | 252/110 |

FOREIGN PATENT DOCUMENTS

| | | | |
|---|---|---|---|
| 140738 | 11/1979 | Japan | 424/70 |
| 169617 | 12/1981 | Japan | 424/70 |
| 46910 | 3/1982 | Japan | 424/70 |
| 2057883 | 4/1981 | United Kingdom | 424/316 |

OTHER PUBLICATIONS

Tsutsumi, Chem. Abs., 1978, vol. 88, pp. 172314p.
Murata et al., Chem. Abs., 1978, vol. 88, pp. 172, 306.

*Primary Examiner*—Dale R. Ore

[57] ABSTRACT

Disclosed are cosmetic compositions for the hair, containing hydrogenated tallow N,N-dimethyl glycinate, in the form of aqueous, alcoholic or aqueous-alcoholic solutions.

7 Claims, No Drawings

HAIR CARE COMPOSITIONS

BACKGROUND OF THE INVENTION

1. Field of the Invention

This invention relates to hair care compositions. More particularly, the invention relates to hair shampoo, hair conditioner, hair spray, and hair setting and styling compositions comprising Hydrogenated Tallow Betaine or its cosmetically acceptable salt as an active ingredient in a suitable carrier.

2. Description of the Prior Art

Hair shampoos contain anionic detergents, as active ingredients, which serve to foam and clean hair. These anionic detergents, while extremely effective in their functions of cleansing and foaming, tend to be harsh to hair's surface, leaving hair in an overly dry, unmanageable state. Furthermore, the hair is rendered susceptible to electrostatic charge accumulation which promulgates the undesirable condition known as fly-away. To mollify these adverse effects, it is the usual practice to incorporate selective ingredients into the shampoo formulation, other than those which contribute to product aesthetics. These selective mollifying additives, while effective in providing greater manageability and hair conditioning, unfortunately interfere with and reduce the anionic detergent's effectiveness in cleansing and foaming.

Hair conditioners and creme rinse preparations, on the other hand, employ cationic surfactants as their key ingredients. These materials, usually quaternary ammonium compounds, are substantive to the negatively charged keratinaceous protein of hair. Because of their substantive properties, treatment of hair with a hair conditioner containing cationic quaternary ammonium compounds (generally after shampooing) provides the hair with a lubricating surface film which allows for easy combing. Hence, knots and tangles, encountered in hair combing after shampooing, are easily dissipated through hair treatment with a cationic hair conditioner. Notwithstanding their desirable characteristics, cationic hair conditioners formulated with quaternary ammonium compounds tend to overcondition the hair, making the hair undesirably heavy, "bodiless" and unattractive in appearance.

Hair setting lotions and hair sprays are usually based upon polymeric resins which provide hair fixative effects. Hair is given rigidity through application of these products enabling the hair to hold a style configuration in place. Plasticizers are also formulated into the product which provide pliability to the films of the polymeric resin coating the hair. The plasticizers allow the resin film to bend, instead of rupturing or breaking, under the stress of slight hair movement. However, the total hair holding potential of the polymeric hair fixative is reduced when plasticizers are incorporated. As a result, the strength of the hair configuration is weakened and the hair style is shortlived.

We have now discovered, surprisingly, that a small amount of a specific amphoteric surfactant, Hydrogenated Tallow Betaine, when incorporated with the key ingredients of a shampoo, cationic hair conditioner, or resinous hair fixative product can offset the incumbent deficiencies of these toiletry products. Hydrogenated Tallow Betaine is compatible with anionic surfactants, cationic surfactants and polymeric resins in their respective formulation environment. It is capable of promoting the favorable properties of those ingredients while sequestering and diminishing any disadvantages imparted to hair.

Certain betaines, as surfactants, are used by the prior art. For example: U.S. Pat. Nos. 3,960,742 and 4,348,292 disclose cleaning and detergent concentrates containing betaines; U.S. Pat. No. 4,166,845 discloses antidandruff compositions containing 10 to 30% by weight of a betaine detergent; and U.S. Pat. No. 4,375,421 pertains to viscous liquids, pastes and gels useful in various cosmetic, toiletry and cleansing compositions containing 5 to 25% by weight of alkylamido betains.

SUMMARY OF THE INVENTION

We have surprisingly discovered that a relatively small amount of Hydrogenated Tallow Betaine can be used to advantage in hair shampoo, conditioner, spray, setting and styling compositions.

Chemically defined, Hydrogenated Tallow Betaine (CTFA designation) is hydrogenated tallow N,N-dimethyl glycinate having the structure

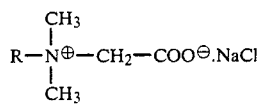

or

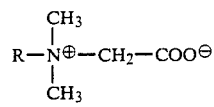

wherein R is hydrogenated tallow alkyl. It is available as a sodium chloride adduct by the Miranol Chemical Co. under the trade name Mirataine TDMB-H. It is a tan, pasty aqueous dispersion having the following typical properties: solids—36% by weight; active betaine—30% by weight, sodium chloride—5.7% by weight; and pH—9.0%. It is hydrophobic and provides high superfatting effects. It can be produced by reacting dimethyl hydrogenated tallow amine (Armak's Armeen DMHTD) with sodium chloroacetate in an aqueous media. The reaction product obtained is hydrogenated tallow N,N-dimethyl glycinate and sodium chloride by-product.

The cosmetic compositions for the hair, containing hydrogenated tallow N,N-dimethyl glycinate, are suitable in the form of aqueous, alcoholic or aqueous-alcoholic solutions (the alcohol preferably being ethanol or isopropanol) or in the form of creams, gels, emulsions, sprays and the like.

The cosmetic compositions for hair, according to the invention, thus include, in particular:

a. Shampoos which contain hydrogenated tallow N,N-dimethyl glycinate (hereinafter called hydrogenated tallow betaine) and at least one anionic surfactant.

Suitable anionic surfactants include the cosmetically acceptable salts of lauryl suflate and lauryl ether sulfate, such as sodium lauryl sulfate, ammonium lauryl sulfate, sodium lauryl ether sulfate and the like.

In these shampoos, the concentration of hydrogenated tallow betaine is from 0.001% to 5% by weight and the concentration of the anionic detergent is generally from 5% to 25% by weight.

The shampoo compositions can also contain various adjuvants such as perfumes, dyestuffs, preservatives, thickeners, foam builders, foam stabilizers, softeners, and one or more cosmetic resins.

The shampoo compositions of the present invention, when applied, attain static-free hair manageability along with unimpaired foaming and cleansing characteristics.

b. Hair conditioners which contain the cationic hair conditioning agent, cetyl trimethyl ammonium chloride, in combination with hydrogenated tallow betaine at ratios from 1,000 parts to 1 part, and preferably 5 parts to 1 part respectively, at combined concentrations of 0.01% to 5% by weight.

The hair conditioner compositions of the present invention, when applied, impart good body to hair while sustaining the snarl-detangling properties characteristic of functional creme rinse hair conditioning products.

c. Hair fixative products which contain at least a polymeric resin in combination with hydrogenated tallow betaine in a ratio from 1 part to 1000 parts, and preferably 1 part to 4 parts of hydrogenated tallow betaine to the polymeric resin at combined concentrations of from 0.1% to 10% by weight.

The polymeric resin utilized in the hair fixative products of the present invention include one or more nonionic polymers of which polyvinylpyrrolidone/vinyl acetate copolymers (PVP/VA) are preferred. Examples of these copolymers are LUVISKOL VA37E and LUVISKOL VA64E. Other suitable polymers include polyvinylpyrrolidone quaternized copolymer having a molecular weight which can exceed 1,000,000. Examples of suitable quaternized copolymers are those marketed under the trade name GAFQUAT 734 (low molecular weight) and GAFQUAT 755 (high molecular weight).

On application of the hair fixative products of the present invention, the hydrogenated tallow betaine acts as an effective plasticizer, yet maintains the maximum potential for hair set holding ability of the polymeric resin.

DETAILED DESCRIPTION OF THE INVENTION

The following Examples further illustrate the present invention.

I. Shampoo Formulas

EXAMPLE 1

| Composition | % w/w |
| --- | --- |
| Sodium lauryl ether sulfate (1 EtO) (Detergent) | 15.0 |
| Hydrogenated tallow betaine | 1.0 |
| Cocamide MEA (Foam Stabilizer) | 3.0 |
| Hydroxyethylcellulose (Thickener) | 0.5 |
| Na$_3$EDTA (Chelating agent) | 0.1 |
| Perfume oil | 0.2 |
| Preservative | 0.1 |
| Color, Water | q.s. 100 |

EXAMPLE 2

| Composition | % w/w |
| --- | --- |
| TEA Lauryl Sulfate (Detergent) | 20.0 |
| Lauryl dimethyl amine oxide (Foam booster) | 2.0 |
| Hydroxypropyl methyl cellulose (Thickener) | 1.0 |
| Na$_2$EDTA (Chelating Agent) | 0.2 |
| Hydrolyzed animal protein-natural | 0.1 |
| Hydrogenated tallow betaine | 2.0 |
| Perfume oil | 0.3 |
| Preservative | 0.2 |
| Color, Water | q.s. 100 |

EXAMPLE 3

| Composition | % w/w |
| --- | --- |
| Ammonium lauryl sulfate (Detergent) | 12.0 |
| Hydrogenated tallow betaine | 0.03 |
| Cocamide DEA (Foam stabilizer) | 3.0 |
| Coco dimethyl amine oxide (Foam Booster) | 5.2 |
| Na$_2$ Hydroxy EDTA (Chelating Agent) | 0.1 |
| PEG-2,000 Monostearate (Thickener) | 2.0 |
| Perfume oil | 0.3 |
| Preservative | 0.1 |
| Color, Water | q.s. 100 |

EXAMPLE 4

| Composition | % w/w |
| --- | --- |
| Sodium lauryl ether sulfate (3 EtO) (Detergent) | 7.5 |
| Sodium lauryl sulfate (Detergent) | 4.5 |
| Hydrogenated tallow betaine | 0.003 |
| Lauramide DEA (Foam stabilizer) | 5.0 |
| PPG-12 Buteth 16 (Viscosity control) | 0.05 |
| Citric acid (pH control) | 0.2 |
| Perfume oil | 1.0 |
| Preservative | 0.125 |
| Color, Water | q.s. 100 |

The shampoo compositions are made by first hydrating resin thickeners, if present, in water. This is followed with the addition of detergents and auxiliary raw materials. The preparations are agitated to uniformity; heat is usually supplied when formulas contain ingredients that are difficult to solubilize. At ambient temperature, to no higher than 45° C., fragrance is mixed in. Color addition, pH, and viscosity adjustments are performed at room temperature. When prepared properly, the shampoos specified should have pH's of 6.0±1.0 and viscosities adjusted to between 2,000 and 3,000 cps. These shampoos produce abundant foam, leave the hair clean and fresh feeling, and surprisingly, produce unexpected manageability and the absence of electrostatic charges.

II. Hair Conditioner Formulas

EXAMPLE 5

| Composition | % w/w |
| --- | --- |
| Cetyl trimethyl ammonium chloride (Quat. hair detangler) | 2.0 |
| Hydrogenated tallow betaine | 0.4 |
| Cetyl alcohol (Conditioning agent) | 0.5 |
| Hydroxyethyl cellulose (Thickener) | 0.75 |
| Citric acid (Acidulant) (pH 5.3) | 0.2 |
| Preservative | 0.1 |
| Color, Fragrance, Water | q.s. 100 |

EXAMPLE 6

| Composition | % w/w |
| --- | --- |
| Stearyl dimethyl benzyl ammonium chloride (Quat. hair detangler) | 1.0 |
| Cetyl trimethyl ammonium chloride | 1.0 |

-continued

| Composition | % w/w |
| --- | --- |
| (Quat. hair detangler) | |
| Hydrogenated tallow betaine | 0.05 |
| Hydrolyzed animal protein-natural | 0.01 |
| Ascorbic acid (Acidulant) (pH 5.5) | 0.3 |
| Ethoxylated stearyl alcohol (20 EtO) (Emulsifier) | 1.5 |
| Preservative | 0.04 |
| Color, Fragrance, Water | q.s. 100 |

EXAMPLE 7

| Composition | % w/w |
| --- | --- |
| Cetyl pyridinium chloride (Quat. hair detangler) | 2.0 |
| Cetyl trimethyl ammonium chloride (Quat. hair detangler) | 0.5 |
| Hydrogenated tallow betaine | 0.1 |
| Ethoxylated cetyl/stearyl alcohol (5 EtO) (Emulsifier) | 0.5 |
| Wheat Germ Oil - natural | 0.01 |
| Hydrochloric acid (Acidulant) (pH 4.4) | 0.02 |
| Hydroxypropyl methyl cellulose (Thickener) | 0.5 |
| Preservative | 0.02 |
| Color, Fragrance, Water | q.s. 100 |

EXAMPLE 8

| Composition | % w/w |
| --- | --- |
| Dicetyl dimethyl ammonium chloride (Quat. hair detangler) | 1.75 |
| Cetyl trimethyl ammonium chloride (Quat. hair detangler) | 0.3 |
| Hydrogenated tallow betaine | 0.003 |
| Stearamidopropyl dimethyl amine (Lipophyle) | 1.25 |
| Ceteary alcohol (Ceteareth 20) (Emulsifier) | 2.0 |
| Cetyl Alcohol (Lipophyle) | 1.0 |
| Hydrolized animal protein - natural | 0.1 |
| PPG Buteth-35 (Viscosity control) | 0.01 |
| Citric Acid (Acidulant) (pH 4.0) | 0.3 |
| Color, Fragrance, Water | q.s. 100 |

The conditioners are manufactured by first hydrating resin thickeners, if present, in a water phase. All other ingredients are added while heating and mixing the preparation. After heating to 65°-75° C., and after ensuring phase uniformity at this temperature, the product is slowly cooled while agitation continues. Fragrance is added at 45° C., agitation continuing. At ambient temperature, color is added; viscosity and pH adjustments are made. All hair conditioner products should have a viscosity range of 1,500–5,000 cps and pH's between 3.5 and 6.5. All preparations gave, as expected, excellent hair detangling and conditioning properties, but surprisingly left hair bouyant, alive with body.

III. Hair Sprays

EXAMPLE 9

| Composition | % w/w |
| --- | --- |
| Gantrez ES-225 (Half ethyl ester of polyvinylmethylether - maleic anhydride) (Resin) | 2.0 |
| Amino methyl propanol (amine neutralizer) | 0.1 |
| Hydrogenated tallow betaine | 0.01 |
| Ethoxylated lanolin alcohols (Plasticizer) | 0.2 |
| Fragrance | 0.1 |
| Methylene chloride (Co-solvent) | 13.3 |

-continued

| Composition | % w/w |
| --- | --- |
| Anhydrous ethanol (Solvent) | q.s. 100 |

EXAMPLE 10

| Composition | % w/w |
| --- | --- |
| Polyvinylpyrrolidone-vinyl acetate (PVP-VA-535) (Resin) | 3.0 |
| Hydrogenated tallow betaine | 0.05 |
| C12–C15 Alcohols benzoate (Plasticizer) | 0.25 |
| Cetyl lactate (Texturizer) | 0.2 |
| Fragrance | 0.1 |
| Methylene chloride (Co-solvent) | 13.3 |
| Anhydrous ethanol (Solvent) | q.s. 100 |

The hair spray concentrates of formulas 9 and 10 are prepared by dissolving the ingredients in their respective solvents and then pressurizing in a suitable aerosol package with hydrocarbon propellant at a ratio of 75 parts by weight concentrate to 25 parts by weight propellant.

IV. Setting Lotions/Styling Aids

EXAMPLE 11

| Composition | % w/w |
| --- | --- |
| Gafquat 755 (Polyquaternium 11) (Hair fixative) | 1.0 |
| PVP (Hair fixative) | 1.0 |
| Hydrogenated tallow betaine | 0.25 |
| Hydrolyzed animal protein - natural | 0.1 |
| Glycerine (Plasticizer) | 0.15 |
| Alcohol (Co-Solvent) | 35.0 |
| Fragrance | 0.1 |
| Color, Water | q.s. 100 |

EXAMPLE 12

| Composition | % w/w |
| --- | --- |
| Polyquaternium 12 (Acrylic hair fixative) | 2.0 |
| Hydrogenated tallow betaine | 0.5 |
| Fragrance | 0.3 |
| Alcohol (Co-solvent) | 30.0 |
| Water | q.s. 100 |

The ingredients of Examples 11 and 12 are dissolved in their respective solvent system and are applied to hair before setting in a style configuration. The product is sprayed onto hair with a pump finger spray; hair is set, dried and combed out.

Hair sprays and setting lotions with hydrogenated tallow betaine provide excellent hair fixative properties for long-lasting hair sets. Yet, they surprisingly show minimum resin "flaking" upon combing of hair which can be attributed to the unique resin plasticizing effects of the hydrogenated tallow betaine. Hair is left full bodied and firm which provide for long-lasting hair sets.

V. Mousse Hair Conditioner; Fixative—Styling Aids

EXAMPLE 13

| Composition | % w/w |
| --- | --- |
| Polyvinylpyrrolidone-Vinyl Acetate (Hair fixative) | 1.25 |
| Polyquaternium 4 (Hair fixative) | 0.3 |

-continued

| Composition | % w/w |
|---|---|
| Hydrogenated tallow betaine | 0.003 |
| Amodimethicone (Cationic silicone conditioner) | 4.0 |
| Octoxynol 9 (Foaming agent) | 1.0 |
| Ascorbic acid (Acidulant) | 0.01 |
| Ethanol (Co-solvent) | 5.0 |
| Water | q.s. 100 |

Formula #13 is a mousse-type styling aid. When packaged in a mousse pressurized container at a ratio of 88 parts formula #13 with 12 parts hydrocarbon propellant, a quick breaking foam is produced which is absorbed into hair and which imparts fixative and conditioning properties. Here too, hydrogenated tallow betaine provides unexpected and desirable plasticizing effects.

While the invention has been described in connection with the preferred embodiments, it is intended to cover alternatives, modifications, and equivalents as may be included within the spirit and scope of the invention as defined by the appended claims.

What is claimed is:

1. A hair shampoo composition comprising by weight:
   a. from 0.001% to 5% of hydrogenated tallow betaine of the formula

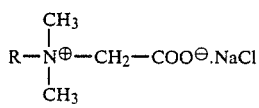

or

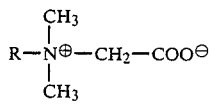

wherein R is hydrogenated tallow alkyl; and about 5% to 25% of at least one anionic surfactant selected from the group consisting of lauryl sulfate, lauryl ether sulfate and the cosmetically acceptable salts thereof and
   b. water q.s. to 100%.

2. A hair conditioner composition comprising:
   a. 1 part of hydrogenated tallow betaine of the formula

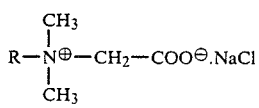

and

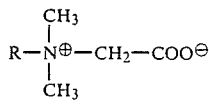

wherein R is hydrogenated tallow alkyl; and
   b. 1000 parts of cetyl trimethyl ammonium chloride wherein the sum of component a and b is from about 0.01% w/w to about 5% w/w based on the total weight of said hair conditioning composition, and
   c. water q.s. to 100%.

3. The hair conditioner composition of claim 2 wherein said hydrogenated tallow betaine is present in said composition in the amount of 1 part to 5 parts of said cetyl trimethyl ammonium chloride.

4. A hair spray composition comprising about 75 parts by weight of a hair spray concentrate and about 25 parts by weight of a hydrocarbon propellant, said hair spray concentrate comprising:
   a. 1 part of hydrogenated tallow betaine of the formula

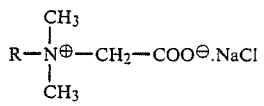

and

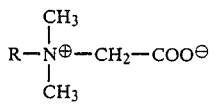

wherein R is hydrogenated tallow alkyl;
   b. 1000 parts of a polymeric resin selected from the group consisting of polyvinylpyrrolidone/vinyl acetate copolymer and polyvinylpyrrolidone quaternised copolymer; wherein the sum of component a and b is from about 0.1% w/w to about 10% w/w based on the total weight of said hair spray concentrate
   c. about 13% by weight of methylene chloride; and
   d. ethanol q.s. to 100% w/w.

5. The hair spray composition of claim 4 wherein said hydrogenated tallow betaine is present in said composition in the amount of 1 part to 4 parts of said polymeric resin.

6. A hair setting/styling lotion comprising:
   a. about 1 part of hydrogenated tallow betaine of the formula

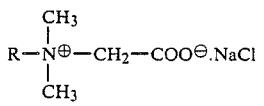

and

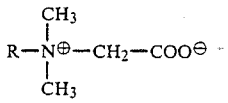

wherein R is hydrogenated tallow alkyl;
   b. about 1000 parts of a polymeric resin selected from the group consisting of polyvinylpyrrolidone/vinyl acetate copolymer and polyvinylpyrrolidone quaternised copolymer; wherein the sum of component a and b is from about 0.1% w/w to about 10% w/w based on the total weight of said hair setting/styling lotion; and
   c. water/ethanol q.s. to 100%.

7. The hair setting/styling lotion of claim 6 wherein said hydrogenated tallow betaine is present in said lotion in the amount of about 1 part to about 4 parts of said polymeric resin.

* * * * *